United States Patent
Selvitelli et al.

(10) Patent No.: US 8,864,719 B2
(45) Date of Patent: Oct. 21, 2014

(54) MEDICAL CARTRIDGE RECEIVER HAVING ACCESS DEVICE

(75) Inventors: David M. Selvitelli, Suffield, CT (US); Melvin A. Finke, DeLand, FL (US); Kathleen Tremblay, Westfield, MA (US)

(73) Assignee: Covidien LP, Mansfield, MA (US)

( * ) Notice: Subject to any disclaimer, the term of this patent is extended or adjusted under 35 U.S.C. 154(b) by 94 days.

(21) Appl. No.: 13/438,854

(22) Filed: Apr. 4, 2012

(65) Prior Publication Data

US 2012/0259287 A1 Oct. 11, 2012

Related U.S. Application Data

(60) Provisional application No. 61/471,909, filed on Apr. 5, 2011.

(51) Int. Cl.
- *A61M 5/24* (2006.01)
- *A61M 39/14* (2006.01)
- *A61M 39/18* (2006.01)
- *A61M 5/00* (2006.01)
- *A61M 5/31* (2006.01)

(52) U.S. Cl.
CPC .............. *A61M 39/18* (2013.01); *A61M 5/2466* (2013.01); *A61M 39/14* (2013.01); *A61M 5/002* (2013.01); *A61M 2005/3118* (2013.01)
USPC ........... 604/201; 606/167; 606/180; 604/200; 604/205; 604/206; 604/89; 604/204; 604/27; 604/38; 604/186; 604/192; 401/133; 401/134

(58) Field of Classification Search
USPC .......... 606/167, 180; 604/200, 205, 206, 411, 604/415, 232, 27, 38, 97.02, 95.01, 124, 604/186–189, 192, 194–199, 220, 224; 401/133, 134; 206/365, 438, 366, 364, 206/571, 370; 141/309; 222/89
See application file for complete search history.

(56) References Cited

U.S. PATENT DOCUMENTS 3,413,974 A 12/1968 Cohen
3,739,779 A * 6/1973 Pfleger .......................... 604/205

(Continued)

FOREIGN PATENT DOCUMENTS

JP 2009-540957 11/2009
WO 2007-149960 A2 12/2007

OTHER PUBLICATIONS

Exam Report issued Oct. 30, 2012 in related Australian Patent Application Serial No. 2012201966, 4 pgs.
English language translation of Notice of Reasons for Rejection mailed May 14, 2013 in corresponding Japanese Patent Application No. 2012-085543, 5 pgs.

(Continued)

*Primary Examiner* — Scott Medway
(74) *Attorney, Agent, or Firm* — Lisa E. Winsor, Esq.

(57) ABSTRACT

A needle and receiver assembly for use with a syringe cartridge filled with medicine includes a cartridge receiver having a hollow interior, an open end sized for receiving at least part of the syringe cartridge, and a closed end opposite the open end. The assembly includes a needle mounted on the receiver having a fluid passage extending between a sharp delivery tip at a distal end of the needle and a sharp access tip at a proximal end of the needle opposite the delivery tip positioned inside the hollow interior of the receiver. The assembly includes a cutter movably mounted in the hollow interior of the receiver for movement relative to the receiver and the needle to cut the diaphragm of the cartridge when received in the hollow interior of the receiver.

9 Claims, 4 Drawing Sheets

(56) References Cited

U.S. PATENT DOCUMENTS

| | | | |
|---|---|---|---|
| 3,825,002 A | | 7/1974 | Paige |
| 3,941,128 A | * | 3/1976 | Baldwin .................. 604/238 |
| 4,019,512 A | * | 4/1977 | Tenczar .................. 604/411 |
| 4,581,023 A | | 4/1986 | Kuntz |
| 5,531,683 A | | 7/1996 | Kriesel et al. |
| 2003/0144633 A1 | | 7/2003 | Kirchhofer |

OTHER PUBLICATIONS

European Search Report dated May 29, 2012 for European Application 12162972.9, 6 pages.

Notice of Rejection dated Aug. 12, 2013 regarding Japanese Patent Application No. 2012-085543, 2 pages, with translation.

Examination Report dated Aug. 28, 2013 regarding Canadian Application No. 2,773,487, 3 pages.

* cited by examiner

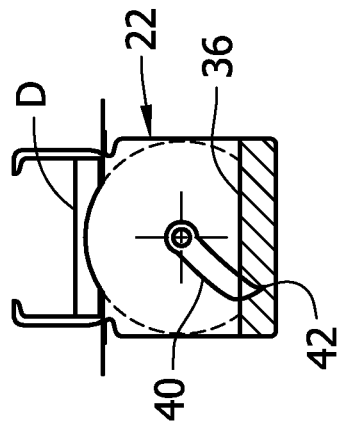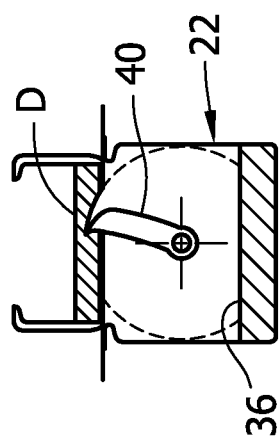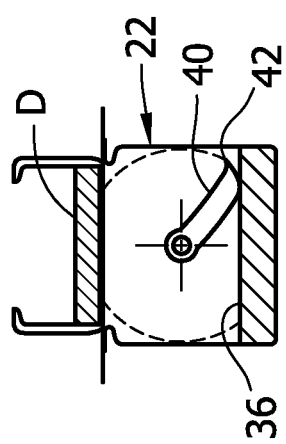

MEDICAL CARTRIDGE RECEIVER HAVING ACCESS DEVICE

CROSS REFERENCE TO RELATED APPLICATION

This application claims priority to U.S. Patent Application 61/471,909 filed Apr. 5, 2011, which is hereby incorporated by reference in its entirety.

BACKGROUND

The present invention generally relates to syringes for injecting liquid medications from prefilled cartridges, and more particularly to a cartridge receiver having a cutter for preparing a cartridge diaphragm.

Local anesthetic is frequently used to numb tissue in a patient's mouth to reduce pain and discomfort a patient may feel during a dental procedure. Conventionally, a reusable syringe assembly is used to inject the anesthetic or medicine from a cartridge or carpule. The cartridge is a glass cylinder containing a local anesthetic and other ingredients. A diaphragm at one end of the cylinder is held in place by an aluminum band. The opposite end of the cylinder has a moveable piston or stopper. The syringe assembly includes a barrel for receiving the cartridge, a plunger rod slidably received in a proximal end of the barrel for actuating the cartridge, an access needle at a distal end of the barrel for puncturing the diaphragm, and a delivery needle connected to the access needle for delivering anesthetic to the patient. In some cases, the plunger rod includes a harpoon for engaging the piston.

Typically, the diaphragm of the cartridge is swabbed with alcohol before being loaded into a pre-sterilized syringe. As the cartridge is loaded into the syringe, the access needle extending proximally from the distal end of the barrel pierces the cartridge diaphragm so the anesthetic in the cartridge can be dispensed. Once the cartridge is in place, the plunger rod of the syringe pushes the piston of the cartridge toward the diaphragm, forcing anesthetic through the access needle, into the delivery needle, and ultimately into the patient.

To assemble the anesthetic syringe assembly the cartridge is swabbed with alcohol, the sterilized syringe is removed from its container, and the alcohol-swabbed cartridge is loaded in the barrel of the syringe. As the plunger moves distally, it forces the cartridge diaphragm onto the access needle and pushes the cartridge piston distally to force the anesthetic through the access needle, through the delivery needle, and ultimately into the patient. As will be appreciated by those skilled in the art, between each use the syringe must be sterilized, a new delivery needle must be mounted on the syringe, and a new cartridge must be prepared and loaded. This multi-step procedure takes time and is resource and labor intensive. There is a need for a syringe assembly that reduces the time, resources, and labor required to provide anesthetic to a patient.

SUMMARY

The present invention relates to a needle and receiver assembly for use with a syringe cartridge filled with medicine. The assembly includes a cartridge receiver that has a hollow interior, an open end sized for receiving at least part of the syringe cartridge, and a closed end opposite the open end. The assembly also includes a needle mounted on the receiver that has a fluid passage extending between a sharp delivery tip at a distal end of the needle adapted for inserting the needle into tissue of a patient and a sharp access tip at a proximal end of the needle opposite the delivery tip adapted for inserting the needle into a diaphragm of the cartridge, the needle extending through the closed end of the receiver so the access tip is positioned inside the hollow interior of the receiver and the delivery tip is positioned outside the receiver. The assembly also includes a cutter movably mounted in the hollow interior of the receiver for cutting the diaphragm of the cartridge when received in the hollow interior of the receiver.

The present invention further relates to a method for preparing a cartridge and a needle and receiver assembly including peeling a protective sheet from a barrier sheet on the receiver to expose adhesive. The method also includes positioning a diaphragm of a cartridge on the exposed adhesive. The method also includes actuating a cutter to remove a portion of the adhesive and diaphragm to expose a sterile area on the diaphragm; capturing the portion of the adhesive and diaphragm. The method also includes piercing the diaphragm with an access tip of a needle.

BRIEF DESCRIPTION OF THE DRAWINGS

FIGS. 3a, 3b, and 3c are schematic cross sections of the assembly of FIG. 1 showing a cutter in different positions;

Corresponding reference characters indicate corresponding parts throughout the drawings.

DETAILED DESCRIPTION OF THE DRAWINGS

Figure 2:
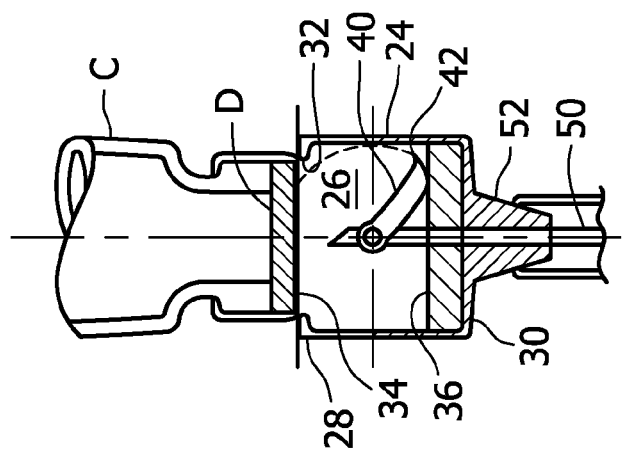
FIG. 2 is a vertical cross section of the assembly of FIG. 1.
Figure 1:
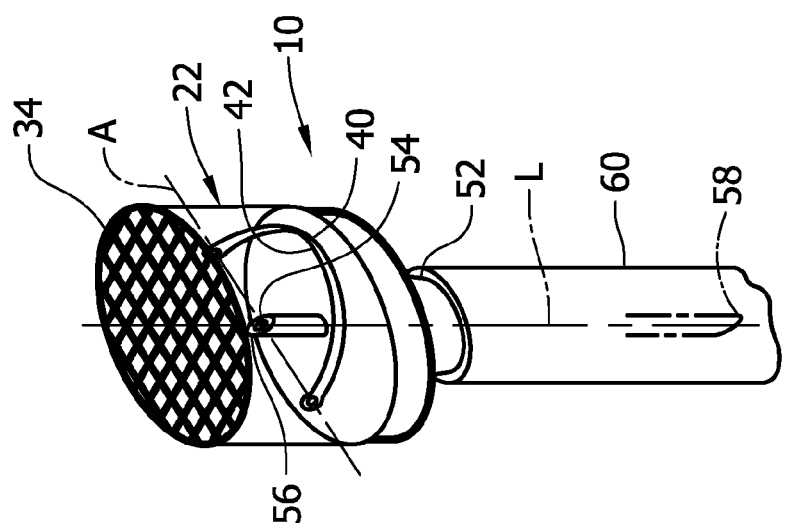
FIG. 1 is a perspective of a needle and receiver assembly of a first embodiment of the present invention.

Referring to the drawings and more particularly to FIG. 1, a needle and cartridge receiver sub-assembly of the present invention is designated in its entirety by the reference number 10. The sub-assembly 10 includes a cartridge receiver, generally designated by 22, as shown in FIG. 1. The cartridge receiver 22 has a cylindrical wall 24 defining a hollow interior 26, an open end 28 sized for receiving part of a conventional syringe cartridge or carpule C, and a closed end 30 opposite the open end as shown in FIG. 2. The open end 28 includes a flange 32 that receives a sterile barrier film 34 having adhesive on both faces. The film 34 closes the open end 28 of the receiver 22 to maintain a sterile environment in the hollow interior 26. The diaphragm D of the cartridge C is adhesively bonded to the barrier 34. A gasket 36 is positioned inside the hollow interior 26 adjacent the closed end 30 of the receiver. A cutter or blade 40 is pivotally attached to the cylindrical wall 24 so that a sharp leading edge 42 of the cutter can rotate in the hollow interior 26, tracing a circular path as indicated by a dashed line in FIG. 2.

As further illustrated in FIG. 2, a needle 50 is mounted on the cartridge receiver 22 so that it extends through a hub 52 formed on the closed end 30 of the receiver. The needle 50 has a central fluid passage 54 (FIG. 1) extending between a sharp delivery tip 58 (shown in phantom in FIG. 1) and a sharp access tip 56 opposite the delivery tip. The delivery tip 58 is positioned at a distal end of the needle 50 and is adapted for insertion in tissue of a patient. The access tip 56 is positioned at a proximal end of the needle 50 and is adapted for piercing the diaphragm D of the cartridge C to insert the needle into the cartridge. The needle 50 extends through the closed end 30 of the receiver 22 so the access tip 56 is positioned inside the hollow interior 26 of the receiver and the delivery tip 58 is positioned outside the receiver. A removable needle sheath 60 is mounted on the needle hub 52 and covers the delivery tip 58 until ready for use to prevent inadvertent injury to medical personnel.

The cutter 40 is a generally C-shaped blade pivotally mounted on opposite sides of the receiver 22 as shown in FIG. 1. Thus, the cutter 40 is rotatably mounted on the receiver 22 for rotation about an axis A extending perpendicular to the longitudinal axis L of the needle and receiver. In one embodiment, the cutter 40 may be rotated by a crank or other actuator (not shown). As the cutter 40 rotates, it progresses through the positions shown in FIGS. 3A, 3B, and 3C. In its initial state, the cutter 40 rests generally against the gasket 36 near the closed end 30 of the receiver 22. When actuated, the cutter 40 pivots upward from the gasket 36 and gouges a generally spherical divot in the diaphragm D of the cartridge C as shown in FIG. 3b. Continuing to rotate, the cutter 40 is buried in the gasket 36 as shown in FIG. 3C so the non-sterile slice removed from the diaphragm D is captured between the cutter and the gasket. In one embodiment, it is envisioned that a pulsing magnetic field could be applied to the cutter 40 to rotate it from the position shown in FIG. 3A, through the position shown in FIG. 3B, and to the position shown in FIG. 3C. Thus, the receiver 22 is positioned in an actuator (not shown) producing an appropriate magnetic field to prepare the needle and receiver sub-assembly 10. The sub-assembly is positioned in a barrel of a syringe and a plunger rod of the syringe is actuated to engage the piston of the cartridge.

To prepare a needle and receiver assembly for use, a protective sheet is peeled from the barrier sheet on the receiver to expose the adhesive. The diaphragm of a cartridge is positioned on the exposed adhesive. Next, the assembly is actuated so the cutter removes a portion of the adhesive and diaphragm to expose a sterile area on the diaphragm. As previously discussed, the removed portions of the adhesive and diaphragm are captured between the cutter and gasket. Once the portion of the diaphragm is removed, the cartridge is advanced toward the access tip of the needle to pierce the diaphragm.

Figure 4:
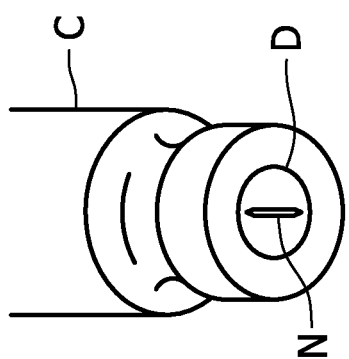
FIG. 4 is a perspective of a syringe cartridge adapted for use with a needle and receiver assembly of a second embodiment of the present invention.
Figure 5A:
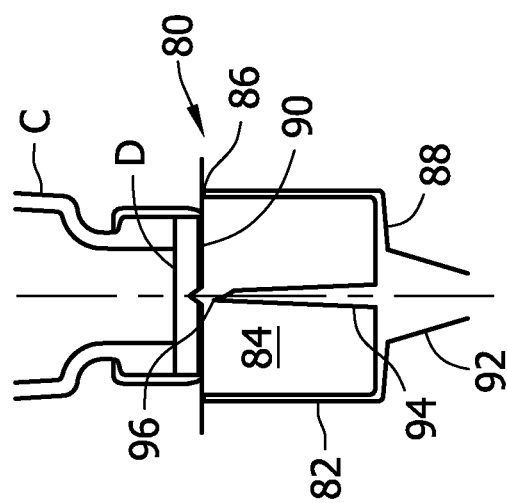
FIGS. 5a and 5b are schematic cross sections of the assembly of FIG. 4 showing the cartridge in different positions.
Figure 5B:
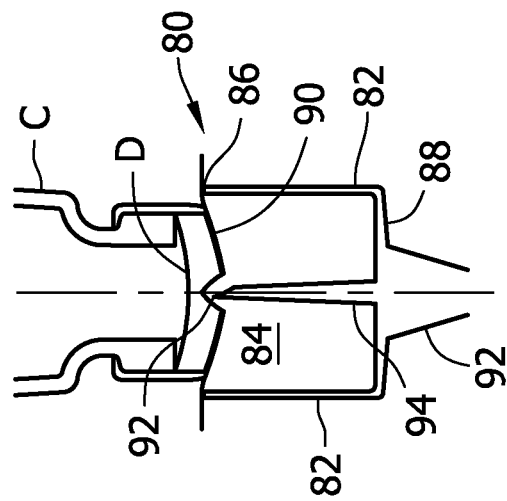

In a second embodiment of the present invention shown in FIG. 4, the diaphragm D of the cartridge C is pre-notched by the manufacturer so the diaphragm is shipped with a frangible notch N. As illustrated in FIG. 5a, the needle and receiver sub-assembly of the second embodiment, generally designated by 80, includes a receiver 82 having a hollow interior 84, an open end 86, and a closed end 88. The open end 86 is covered by a barrier 90 having an adhesive outer face. The closed end 88 has a hub 92 for supporting a needle 94 having a central passage not shown) extending between a sharp distal delivery tip (not shown) and a sharp proximal access tip 96 opposite the delivery tip. Rather than having a cutter, the cartridge C is applied to the sterile barrier 90 as shown in FIG. 5a. The cartridge C is forced through the position shown in FIG. 5b to seat the cartridge against the closed end 88 of the receiver 82. The sub-assembly is positioned in the barrel of the syringe and the plunger rod of the syringe is pushed to engage the piston of the cartridge C. As the plunger rod is pressed against the piston, pressure builds inside the cartridge causing the diaphragm to bulge and forcing the cartridge distally, stretching the sterile barrier. Both apply a radial force to the cartridge notch, tearing the diaphragm at the notch and exposing a portion of the diaphragm D. As the cartridge continues to move distally, the access tip 96 of the needle 94 pierces the newly exposed portion of the diaphragm D. The non-sterile portions of the diaphragm D are captured against the sterile barrier 90 of the sub-assembly 80 to prevent contamination of the fluid delivered through the needle 94. As other aspects of the second embodiment are similar to those of the first embodiment, the second embodiment will not be described in further detail.

Figure 7B:
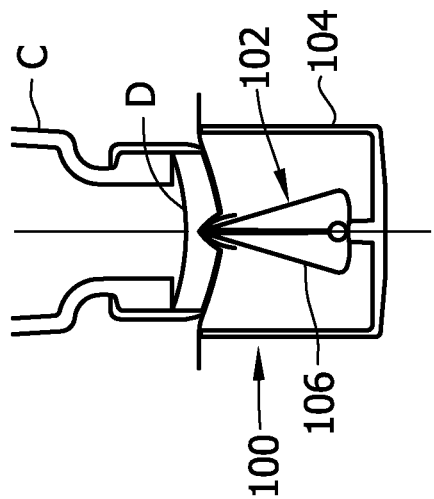
FIGS. 7a and 7b are schematic cross sections of the assembly of FIG. 4 showing the cartridge in different positions.
Figure 7A:
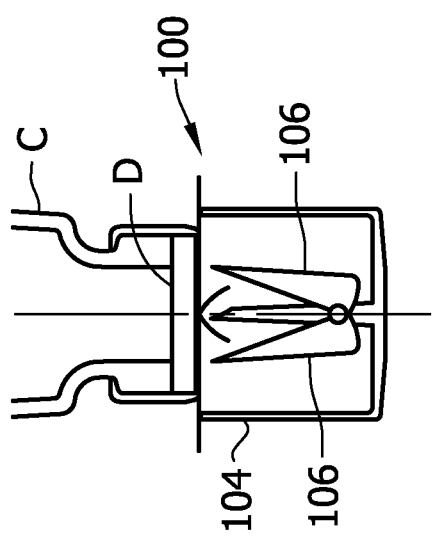
Figure 6:
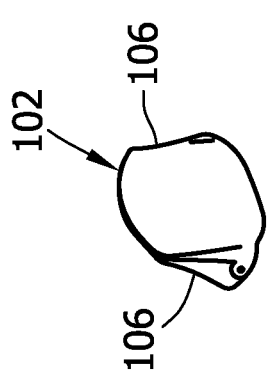
FIG. 6 is a perspective of a cutter of an assembly of a third embodiment of the present invention.

A third embodiment of a needle and receiver sub-assembly of the present invention is designated in its entirety by the reference number 100 in FIG. 7a. The sub-assembly 100 of the third embodiment is similar to that of the first embodiment except a different cutter, generally designated by 102, is mounted inside its receiver 104. The cutter 102 comprises two opposing blades 106 as shown in FIG. 6 pivotally attached to the receiver 104. The opposing blades 106 of the cutter 102 are configured such that they initially engage each other. When the plunger rod is depressed, the cartridge C moves distally into the receiver 104. The blades 106 cut through the sterile barrier and into the diaphragm D. As the cartridge continues to travel distally, the cutters separate, skiving the non-sterile surface of the diaphragm away with each cutter, exposing its internal sterile surface positioned directly above the access end of the needle. As other features of the third embodiment are similar to those of the first embodiment, they will not be described in further detail.

As will be apparent to those skilled in the art, various materials may be used to make the components of the needle and receiver sub-assemblies. For example, the needles and cutters may be made of stainless steel, and the receivers may be made of plastic. Further, the receivers may be made transparent so that flash back can be visually confirmed.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A needle and receiver assembly for use with a syringe cartridge filled with medicine, said assembly comprising:
   a cartridge receiver having a hollow interior, an open end sized for receiving at least part of the syringe cartridge, and a closed end opposite the open end;
   a needle mounted on the receiver having a fluid passage extending between a delivery tip at a distal end of the needle for inserting the needle into tissue of a patient and an access tip at a proximal end of the needle opposite the delivery tip for inserting the needle into a diaphragm of the cartridge, the needle extending through the closed end of the receiver so the access tip is positioned inside the hollow interior of the receiver and the delivery tip is positioned outside the receiver; and
   a cutter movably mounted in the hollow interior of the receiver for movement relative to the receiver and the needle to cut the diaphragm of the cartridge when received in the hollow interior of the receiver.

2. An assembly as set forth in claim 1 wherein the cutter is rotatably mounted on the receiver for rotation about an axis of rotation extending perpendicular to a longitudinal axis of the needle.

3. An assembly as set forth in claim 2 further comprising an actuator for rotating the cutter to cut the diaphragm of the cartridge.

4. An assembly as set forth in claim 1 further comprising a gasket positioned inside the hollow interior of the receiver adjacent the closed end.

5. An assembly as set forth in claim 4 wherein the cutter engages the gasket after cutting the diaphragm to hold a cut piece of the diaphragm against the gasket.

6. An assembly as set forth in claim 1 further comprising a barrier sheet extending across the open end of the receiver for maintaining a sterile environment inside the hollow interior of the receiver before use.

7. An assembly as set forth in claim 6 wherein the barrier sheet includes an adhesive for adhering to the diaphragm of the cartridge.

8. An assembly as set forth in claim 1 wherein the cutter comprises a pair of opposing blades moveable away from each other for skiving a non-sterile surface of the diaphragm.

9. A system, comprising an assembly as set forth in claim 1, further comprising a cartridge received by the assembly.

* * * * *